United States Patent [19]

Oshlack

[11] Patent Number: 4,861,598

[45] Date of Patent: Aug. 29, 1989

[54] CONTROLLED RELEASE BASES FOR PHARMACEUTICALS

[75] Inventor: Benjamin Oshlack, New York, N.Y.

[73] Assignee: Euroceltique, S.A., Luxembourg

[21] Appl. No.: 887,340

[22] Filed: Jul. 18, 1986

[51] Int. Cl.⁴ .......................... A61K 9/22; A61K 9/26
[52] U.S. Cl. .................................... 424/468; 424/469;
424/470; 424/486; 424/487; 424/501; 424/502
[58] Field of Search ............... 424/468, 469, 470, 486, 424/487, 501, 502

[56] References Cited

U.S. PATENT DOCUMENTS

| | | | |
|---|---|---|---|
| 3,965,256 | 6/1976 | Leslie | 424/470 |
| 4,263,273 | 4/1981 | Appelgren et al. | 424/497 |
| 4,341,759 | 7/1982 | Bogentoft et al. | 424/497 |
| 4,443,428 | 4/1984 | Oshlack et al. | 424/468 |
| 4,562,061 | 12/1985 | Appelgren et al. | 424/497 |
| 4,600,577 | 7/1986 | Didriksen | 424/497 |
| 4,708,874 | 11/1987 | De Haan et al. | 424/470 |

FOREIGN PATENT DOCUMENTS 0040590 11/1981 European Pat. Off. .

OTHER PUBLICATIONS

Fassihi, C.A. 106, #55797c (1987) of Int. J. Pharm. (1986), 34 (1-2): 169-172.
Bogentoft, C.A. 96, #57792w (1982) of E.P.O. 40590, 25 Nov. 1981.

Primary Examiner—Shep K. Rose
Attorney, Agent, or Firm—Steinberg & Raskin

[57] ABSTRACT

The release of therapeutically active agents from controlled release bases is extended by using a combination of a higher aliphatic alcohol and an acrylic resin as the base material.

10 Claims, No Drawings

CONTROLLED RELEASE BASES FOR PHARMACEUTICALS

BACKGROUND OF THE INVENTION

It is known in the pharmaceutical art to prepare compositions which provide for slow release of pharmacologically active substances contained in said compositions after oral administration to humans and animals. Such slow release compositions are used to delay absorption of a medicament until it has reached certain portions of the alimentary tract. Such controlled release of a medicament in the alimentary tract further maintains a desired concentration of said medicament in the blood stream for a longer duration than would occur if conventional rapid release dosage forms are administered.

Slow release formulations known in the art include specially coated pellets, coated tablets and capsules wherein the slow release of the active medicament is brought about through selective breakdown of the coating of the preparation or through compounding with a special matrix to affect the release of a drug. Some slow release formulations provide for related sequential release of a single dose of an active compound at predetermined periods after administration.

It is the intent of all slow release preparations to provide a longer period of pharmacologic response after the administration of the drug and is ordinarily experienced after the administration of the rapid release dosage forms. Such longer periods of response provides for many inherent therapeutic benefits that are not achieved with corresponding short acting, immediate release preparations. Thus, therapy may be continued without interrupting the sleep of the patient, which is of special importance when treating an epileptic patient to prevent nocturnal seizures, or for those patients who experience migraine headaches on awakening, as well as for the debilitated patient for whom uninterrupted sleep is essential.

Another critical role for extending acting medications is in therapy of cardiovascular diseases whereby optimal peak blood levels of a medicament must be maintained at the steady state level to achieve the desired therapeutic effect. Unless conventional rapid acting drug therapy is carefully administered at frequent intervals to maintain effective steady state blood levels of the drug, peaks and valleys in the blood level of the active drug occurs because of the rapid absorption, systemic excretion of the compound and through metabolic inactivation, thereby producing special problems in maintenance therapy of the patient. A further general advantage of longer acting drug preparations is improved patient compliance resulting from the avoidance of missed doses through patient forgetfulness.

The prior art teaching of the preparation and use of compositions providing the slow release of an active compound from a carrier is basically concerned with the release of the active substance into the physiologic fluid of the alimentary tract. However, it is generally recognized that the mere presence of an active substance in the gastrointestinal fluids does not, by itself, insure bioavailability. Bioavailability, in a more meaningful sense, is the degree, or amount, to which a drug substance is absorbed to be available to a target tissue site after administration of a unit dosage form.

To be absorbed, and active drug substance must be in solution. The time required for a given proportion of an active drug substance contained in unit dosage form to enter into solution in appropriate physiologic fluids is known as the dissolution. The dissolution time of an active substance from a unit dosage form is determined as the proportion of the amount of active drug substance released from a unit dosage form over a specified time base by a test method conducted under standardized conditions. The physiologic fluids of the gastrointestinal tract are the media for determining dissolution time. The present state of the art recognizes many satisfactory test procedures to measure dissolution time for pharmaceutical compositions, and these test procedures are described in official compendia world wide.

Although there are many diverse factors which influence the dissolution of drug substance from its carrier, the dissolution time determined for a pharmacologically active substance from the specific composition is relatively constant and reproducible. Among the different factors affecting the dissolution time are the surface area of the drug substance presented to the dissolution solvent medium, the pH of the solution, the solubility of the substance in the specific solvent medium, and the driving forces of the saturation concentration of dissolved materials in the solvent medium. Thus, the dissolution concentration of an active drug substance is dynamically modified in its steady state as components are removed from the dissolution medium through absorption across the tissue site. Under physiologic conditions, the saturation level of the dissolved materials is replenished from the dosage form reserve to maintain a relatively uniform and constant dissolution concentration in the solvent medium providing for a steady state absorption.

The transport across a tissue absorption site of the gastrointestinal tract is influenced by the Donnan osmotic equilibrium forces on both sides of the membrane since the direction of the driving force is the difference between the concentrations of active substance on either side of the membrane, i.e. the amount dissolved in the gastrointestinal fluids and the amount present in the blood. Since the blood levels are constantly being modified by dilution, circulatory changes, tissue storage, metabolic conversion and systemic excretion, the flow of active materials is directed from the gastrointestinal tract into the blood stream.

Notwithstanding the diverse factors influencing both dissolution and absorption of a drub substance a strong correlation has been established between the in-vitro dissolution time determined for a dosage form and the in-vivo bioavailability. This correlation is so firmly established in the art that dissolution time has become generally descriptive of bioavailability potential for the active component of the particular unit dosage composition. In view of this relationship, it is clear that the dissolution time determined for a composition is one of the important fundamental characteristics for consideration when evaluating slow release compositions.

Slow release pharmaceutical compositions have generally been prepared with the sustained release matrix comprising hydroxyalkyl cellulose components and higher aliphatic alcohols as described in U.S. Pat. No. 4,235,870. While such sustained release matrix compositions have constituted a definite advance in the art, improvements in these compositions have been sought, and improvements are particularly required where the active pharmaceutical material is highly water soluble.

SUMMARY OF THE INVENTION

It is accordingly a primary object of the present invention to provide for new sustained release bases which extend the time of release of active medicaments incorporated therein.

It is another object of the present invention to provide new sustained release bases for pharmaceutical compositions which provide extended release time for active medicaments, and which are particularly useful where the active medicament is highly water soluble.

It is yet another object of the present invention to provide sustained release base compositions which are useful for all types of pharmaceutically active ingredients and which can extend the time of release of all such ingredients.

Other objects and advantages of the present invention will be apparent from the further reading of the specification and of the appended claims.

With the above and other objects in view, the present invention mainly comprises compositions for controlled slow release of therapeutically active ingredients over a predetermined or a specified period of time, comprising as the base composition a combination of a higher aliphatic alcohol and an acrylic resin. Base compositions prepared from such higher aliphatic alcohols and acrylic resins provide sustained release of therapeutically active ingredients over a period of time from five hours and for as much as 24 hours after administration, generally oral administration, in humans or animals.

The bases of the present invention are prepared from any pharmaceutically acceptable higher aliphatic alcohol, the most preferred being fatty alcohols of 10-18 carbon atoms, particularly stearyl alcohol, cetyl alcohol, cetostearyl alcohol, lauryl alcohol, myristyl alcohol and mixtures thereof.

Any acrylic polymer which is pharmaceutically acceptable can be used for the purposes of the present invention. The acrylic polymers may be cationic, anionic or non-ionic polymers and may be acrylates, methacrylates, formed of methacrylic acid or methacrylic acid esters. These polymers can be synthesized, as indicated above, to be cationic, anionic or non-ionic, which then renders the polymers that would be pH dependent and consequently soluble in, or resistant to solutions over a wide range in pH. The most available of the acrylic polymers for the purposes of the present invention are those that are marketed under the trade name "EUDRAGIT" and are available from Rohm Pharma. GmbH, Weiterstat, West Germany.

In preparing tablets or the like from the bases of the present invention, other excipients may be used, these being typically inert auxillary materials used in the art of tableting or capsule filling, and can include, for example, binders, such as polyvinyl pyrroldine, fillers, such as lactose, disintegrants, such as corn starch, and lubricants such as magnesium stearate.

In preparing the matrices of the present invention, the two basic materials, namely the higher aliphatic alcohol and the acrylic resin, are combined together using a wet (aqueous or organic) granulation technique of at least one step, to form a uniform granulate together with any of the other excipients that are required for the tableting or the capsule filling. One or more therapeutic agents can be combined during the process of preparing the granulate, or mixed with the granulate after it is prepared.

The granulation is generally prepared using the "wet" granulating method, that is, most of the excipients with (or without) the therapeutic agent or agents are combined together with a granulating fluid until a moist granular mass is obtained. The mass is then dried until only trace amounts of fluid remain in the granulate as residual moisture. The granulate is then sized using a suitable screening device, which then provides a flowable powder which can then be filled into capsules or compressed into matrix tablets or caplets. It has unexpectedly been found that the combination of the higher aliphatic alcohol and the acrylic polymer has a synergistic action with respect to delaying the release of the therapeutically active ingredient. This phenomenon is of particular advantage when the active material is highly water soluble.

It has been observed that when desiring to control the release of some highly water soluble pharmacologically active ingredients, for example oxycodone, from conventional controlled release tablet matrices, a delay or gradual release of such material can be difficult to achieve. However, when such highly water soluble pharmacologically active material such as oxycodone is incorporated into the matrix system of the present invention, a controlled release of the material is clearly observable. The method used to measure the control of release is the dissolution technique as described in USP XXI.

In the composition of higher aliphatic alcohol and acrylic resin for controlled release bases in accordance with the present invention, the amount of acrylic resin is preferably between 10-60% (based on the total of acrylic resin and aliphatic alcohol), more preferably 15-40%, and most preferably about 20-35%. All percentages are by weight.

It has been found that when using the acrylic resins in combination with the higher aliphatic alcohol, the preferred acrylic resin being those sold under the trade name Eudragit, and preferably the Eudragit RL, RS, S, E30D, and L30D, there was unexpectedly a potentiation of the control of the drug release properties for the flow and controlled release of medicaments. This potentiation of action is particular apparent in the case of the use of a highly water soluble therapeutic agent.

Using the combination of the aliphatic alcohol and acrylic resin as the base for therapeutic agents results in optimum control of drug release, utilizing the matrix base of the present invention in a range of 20-40% by weight of the total weight of the selected dosage unit, and a delay in retardation of generally 5-12 hours, and up to 24 hours and be achieved. The lower part of the range of amount of base generally exhibits a release rate of 5 hours, and as the weight percentage of the controlled release base increases, the delay of drug release also increases.

DESCRIPTION OF PREFERRED EMBODIMENTS

The following examples are given to further illustrate the present invention. The scope of the invention is not, however, meant to be limited to the specific details of the examples.

EXAMPLE I

The bronchodilator drug, Aminophylline, (which is the ethylene diamine salt of theophylline) was tested in the slow release system of the invention.

It was desired to prepare a controlled release Aminophylline tablet containing 225 mg active ingredient.

The following three tablets demonstrate the principles of the invention, the applicability and the advantages for pharmaceutical use.

| INGREDIENT | FORMULATION (A) | FORMULATION (B) | FORMULATION (C) |
|---|---|---|---|
| Aminophylline | 225.0 mg | 225.0 mg | 115.0 mg |
| P.V.P. | 3.4 mg | 3.4 mg | 3.4 mg |
| Eudragit RS | — | 10.0 mg | 20.0 mg |
| Acetone/Isoproplyl alcohol | q.s. | q.s. | q.s. |
| Cetostearyl Alcohol | 86.6 mg | 76.6 mg | 66.6 mg |
| Magnesium Stearate | 2.4 mg | 2.4 mg | 2.4 mg |
| Talc | 6.0 mg | 6.0 mg | 6.0 mg |
|  | 323.4 mg | 323.4 mg | 323.4 mg |

The tablets were prepared according to the following method:

The aminophylline and P.V.P. were intimately mixed in a suitable mixing apparatus. The Eudragit RS (in the case of tablets B and C) was dissolved in the acetone/isopropyl alcohol (50:50 ratio) which was used as the granulating fluid. Whilst the powders were mixing, the granulating fluid was incorporated into the mixing powders until a moist granular mass was obtained. This was then dried and after drying screened through a 12 mesh screen. The required quantity of cetostearyl) alcohol was melted (at approx. 60°-70°) and using suitable mixing apparatus, then incorporated into the warm granular mass. After cooling, the granulate was screened again through a 12 mesh screen. The lubricants (talc, magnesium stearate) were then mixed into the granulate.

The tablets were compressed on a suitable tabletting machine using round biconvex tooling of 12/32″ in diameter.

Dissolution results, using USP paddle 100 rpm, in simulated gastric fluid for the first hour, and thereafter in simulated intestinal fluid were as follows:

| | % AMINOPHYLLINE DISSOLVED | | |
|---|---|---|---|
| HOUR | FORMULATION (A) | FORMULATION (B) | FORMULATION (C) |
| 1 | 19.1% | 20.1% | 19.2% |
| 2 | 77.5% | 47.0% | 40.2% |
| 3 | 100.0% | 67.2% | 55.0% |
| 4 | | 84.0% | 67.7% |
| 6 | | 100.0% | 82.0% |
| 8 | | | 93.0% |
| 9 | | | 100.0% |

From the above dissolution results, it can be seen that when approximately 15% (10 mg/tablet) of the cetostearyl alcohol was replaced with the acrylic resin there was an extension of the time of release of 100% of the Aminophylline from three hours to six hours, and when the percentage replacement with acrylic resin was increased from 15% to 30% (that is 20 mg per tablet), there was a further extension of 100% Aminophylline released over a nine hour period.

EXAMPLE II

The usefulness of the invention was further demonstrated by the preparation of a controlled release tablet of the narcotic analgesic, oxycodone.

It was desired to produce an oxycodone controlled release tablet which would show a controlled gradual release of active material over an approximate 9 to 10 hour period. The following tablets were prepared.

| | Mg/tablet | |
|---|---|---|
| Ingredient | Formulation A | Formulation B |
| Oxycodone | 9.2 mg | 9.2 mg |
| Lactose | 200.0 mg | 200.0 mg |
| Eudragit E30D (Solids) | — | 11.2 mg |
| Water | q.s. | — |
| Stearyl alcohol | 61.2 mg | 50.0 mg |
| Stearic acid | 5.3 mg | 5.3 mg |
| Talc | 5.3 mg | 5.3 mg |
|  | 281.0 mg | 281.0 mg |

These tablets were prepared according to the following method:

The oxycodone and lactose were intimately mixed in a suitable mixer. A granulation was then prepared by incorporating the granulating fluid into the mixing powders. In the case of tablet A, the granulating fluid was water. In the case of tablet B, the granulating fluid was the acrylic suspension "Eudragit E30D", which is a 30% aqueous suspension of the acrylic resin, and the quantity of suspension used was the quantity equivalent to 11.2 mg/tablet of solid resin substance. The granulate was then dried and passed through a 12 mesh screen. The stearyl alcohol was melted and incorporated into the warm granules using a suitable mixer. After cooling, the granules were passed through a 12 mesh screen. The granules were lubricated by mixing in the talc and stearyl alcohol. Tablets were then compressed on a suitable tabletting machine using round biconvex tooling 10/32″ in diameter.

Dissolution results, using U.S.P. paddle, 100 r.p.m., in simulated gastric fluid for the first hour, and thereafter in simulated intestinal fluid, were as follows:

| | % OXYCODONE DISSOLVED | |
|---|---|---|
| HOUR | TABLET A | TABLET B |
| 1 | 43.% | 16.% |
| 2 | 83.% | 51.% |
| 3 | 91.% | 64.% |
| 4 | 97.% | 70.% |
| 5 | 100.% | 76.% |
| 6 | | 78.% |
| 8 | | 96.% |
| 9 | | 100.% |

When comparing the dissolution results of tablets A and B, it was observed that when approximately 20% (11.2 mg/tablet) of the cetostearyl alcohol was replaced with Eudragit E 30D (as solids in the final formulation), there was a potentiation of the control of the release of the oxycodone from the tablet formulation, from 100% released in five hours to a 100% release in nine hours.

EXAMPLE III

It was desired to prepare a slow release preparation of the beta-adrenergic blocking agent "propranolol", to have a 100% in gradual release of the active drug over a nine hour period. To demonstrate the effectiveness of the invention the following tablet formulations (using the production method cited in example I above) were prepared:

| INGREDIENT | Mg/tablet FORMULATION A | FORMULATION B |
| --- | --- | --- |
| Propranolol | 30.0 | 30.0 |
| Lactose | 91.5 | 91.5 |
| Eudgragit S | — | 8.0 |
| Granulating fluid (acetone/IPA/H₂O) | q.s. | q.s. |
| Cetostearyl alcohol | 24.0 | 16.0 |
| Talc | 3.0 | 3.0 |
| Magnesium Stearate | 1.5 | 1.5 |
| | 150.0 mg | 150.0 mg |

These tablets were compressed using round biconvex tooling of 9/32" in diameter.

The tablets were then tested for dissolution using the USP basket, 100 r.p.m., in simulated gastric fluid for the first hour, and thereafter using simulated intestinal The results for the dissolution were as follows:

| | % PROPRANOLOL DISSOLVED | |
| --- | --- | --- |
| HOUR | FORMULATION A | FORMULATION B |
| 1 | 46.4 | 36.4 |
| 2 | 70.4 | 55.8 |
| 3 | 84.5 | 67.7 |
| 4 | 94.4 | 78.3 |
| 5 | 100.0 | 84.3 |
| 6 | — | 90.4 |
| 8 | — | 96.0 |
| 9 | — | 100.0 |

Thus we can observe that by substituting 33% of the cetostearyl alcohol in formula A with the acrylic resin, a potentiation of controlled release of the Propranolol is seen. There is a further delay and extension of the dissolution time by 4 hours, to 100% release over a nine hour period.

EXAMPLE IV

The narcotic drug Morphine is very effective for pain relief, and in the care of terminal cancer, a controlled release tablet, releasing the morphine slowly over many hours is particularly suitable. The following two tablets demonstrate the principles of the invention, and applicability of the incorporation of morphine into such a tablet allowing a controlled release of active drug over many hours.

| INGREDIENT | Mg/tablet FORMULATION A | FORMULATION B |
| --- | --- | --- |
| Morphine Sulphate | 30.0 mg | 30.0 mg |
| Lactose | 79.5 mg | 79.5 mg |
| Eudragit RL | — | 12.0 mg |
| Acetone/Isopropyl-alcohol | q.s. | q.s. |
| Stearyl Alcohol | 36.0 mg | 24.0 mg |
| Talc | 3.0 mg | 3.0 mg |
| Magnesium Steareate | 1.5 mg | 1.5 mg |
| | 150.0 mg | 150.0 mg |

The tablets were prepared according to the method referred to in Example I.

This dissolution of the tablets (USP method is described in the previous examples) were as follows:

| | % MORPHINE DISSOLVED | |
| --- | --- | --- |
| HOUR | FORMULATION A | FORMULATION B |
| 1 | 31.8% | 35.7% |
| 2 | 48.9% | 49.3% |
| 3 | 62.6% | 55.9% |
| 4 | 72.5% | 61.4% |
| 6 | 84.3% | 66.5% |
| 8 | 100.0% | 72.2% |
| 12 | — | 82.8% |
| 18 | — | 100.0% |

We can thus see that when 33% of the cetostearyl alcohol is replaced by the acrylic resin that we have an extension of dissolution time from 100% drug release in eight hours to eighteen hours. This extended slow release of morphine would thus make this tablet even suitable for a once a day administration.

While the invention has been illustrated with respect to particular formulations of higher aliphatic alcohol and acrylic resin, and with respect to particular therapeutic agents, it is apparent that variations and modifications thereof can be made without departing from the spurt or scope of the invention. Such modifications are meant to be comprehended within the scope and equivalence of the appended claims.

What is claimed is:

1. Extended action controlled release pharmaceutical composition for oral administration, comprising a pharmaceutically effective amount of a pharmaceutically active agent distributed in a controlled release core or matrix comprising a higher aliphatic alcohol of 10–18 carbon atoms and a pharmaceutically acceptable acrylic resin, said acrylic resin being in an amount of about 10–60% by weight of the weight of said higher aliphatic alcohol plus said acrylic resin wherein said pharmaceutical agent is amitryptaline, atropine, chlorpheniramine, chlorpromizine, codeine, dexbrompheniramine, diphenylhydramine, doxilamine, ephedrine, hyoscyamine, morphine, oxycodone, papavarine, phenylpropanolamine, propranolol, quinidine, scoplamine or thioridazine.

2. Pharmaceutical composition according to claim 1 wherein said acrylic resin is an amount of about 15–40% by weight.

3. Pharmaceutical composition according to claim 1 wherein said acrylic resin is in amount of about 20–35% by weight.

4. Pharmaceutical composition according to claim 1 wherein said core or matrix also includes a binder in an amount sufficient to bind said composition.

5. Pharmaceutical composition according to claim 4 wherein said core or matrix also includes a filler.

6. Pharmaceutical composition according to claim 5 wherein said core or matrix also includes a disintegrant in a disintegrant effective amount.

7. Pharmaceutical composition according to claim 6 wherein said core or matrix also includes a lubricant.

8. Pharmaceutical composition according to claim 1 wherein said core or matrix constitutes about 20–40% by weight of said composition.

9. Pharmaceutical composition according to claim 1 wherein said pharmaceutically active agent is highly water soluble.

10. Pharmaceutical composition according to claim 1 wherein said pharmaceutical agent is oxycodone.

* * * * *